United States Patent

Shim

[11] Patent Number: 5,823,991
[45] Date of Patent: Oct. 20, 1998

[54] PENILE ERECTION ASSIST DEVICE AND METHOD

[76] Inventor: Youngtack Shim, 3905 Springstop La., Durham, N.C. 27705

[21] Appl. No.: 690,123

[22] Filed: Jul. 31, 1996

[30] Foreign Application Priority Data

Jul. 31, 1995 [KR] Rep. of Korea ................ 1995 23498

[51] Int. Cl.$^6$ .................................................. A61M 31/00
[52] U.S. Cl. ................................ 604/49; 604/93; 604/48; 600/40
[58] Field of Search ........................ 604/49, 116, 891.1, 604/48, 93, 104, 131

[56] References Cited

U.S. PATENT DOCUMENTS

| | | | |
|---|---|---|---|
| 4,724,830 | 2/1988 | Fischell | 600/40 X |
| 4,871,351 | 10/1989 | Feingold | 604/66 |
| 4,978,338 | 12/1990 | Melsky et al. | 604/93 |
| 5,197,322 | 3/1993 | Indravudh | 73/3 |
| 5,250,020 | 10/1993 | Bley | 600/40 |
| 5,263,981 | 11/1993 | Polyak et al. | 623/12 |
| 5,328,460 | 7/1994 | Lord et al. | 604/67 |
| 5,344,388 | 9/1994 | Maxwell et al. | 600/40 |
| 5,360,407 | 11/1994 | Leonard | 604/116 X |
| 5,433,694 | 7/1995 | Lim | 600/38 |
| 5,437,605 | 8/1995 | Helmy | 600/40 |
| 5,507,737 | 4/1996 | Palmskog | 604/93 X |
| 5,509,891 | 4/1996 | DeRidder | 600/39 |
| 5,514,103 | 5/1996 | Srisathapat et al. | 604/141 |
| 5,575,770 | 11/1996 | Milsky et al. | 604/93 |
| 5,643,207 | 7/1997 | Rise | 604/93 |

OTHER PUBLICATIONS

Brochure "MiniMed 506 Insulin Pump"; MiniMed Technologies; Jan. 1994.

*Primary Examiner*—Mark Bockelman
*Assistant Examiner*—N. Kent Gring
*Attorney, Agent, or Firm*—Myers Bigel Sibley & Sajovec P.A.

[57] ABSTRACT

A penile erection assist method and apparatus treats male impotence by providing physiologically active vasodilating drugs to the penile erectile tissues in a manner which minimizes pain therein. The penile erection assist device includes an implantable storage unit which is implanted remote from sensitive penile tissue. The drug is delivered to the penile erectile tissue through sterile thin tubing which is implanted into the patients body with the proximal end in fluid communication with the storage unit and the distal end configured to be positioned adjacent proximal penile erectile tissues. This configuration advantageously preserves the intact function of penile erectile tissues by minimally intruding therein. Further, the device and method can be employed with patients having various etiologic origins whether the need is acute or permanent, according to the needs of the patient.

24 Claims, 9 Drawing Sheets

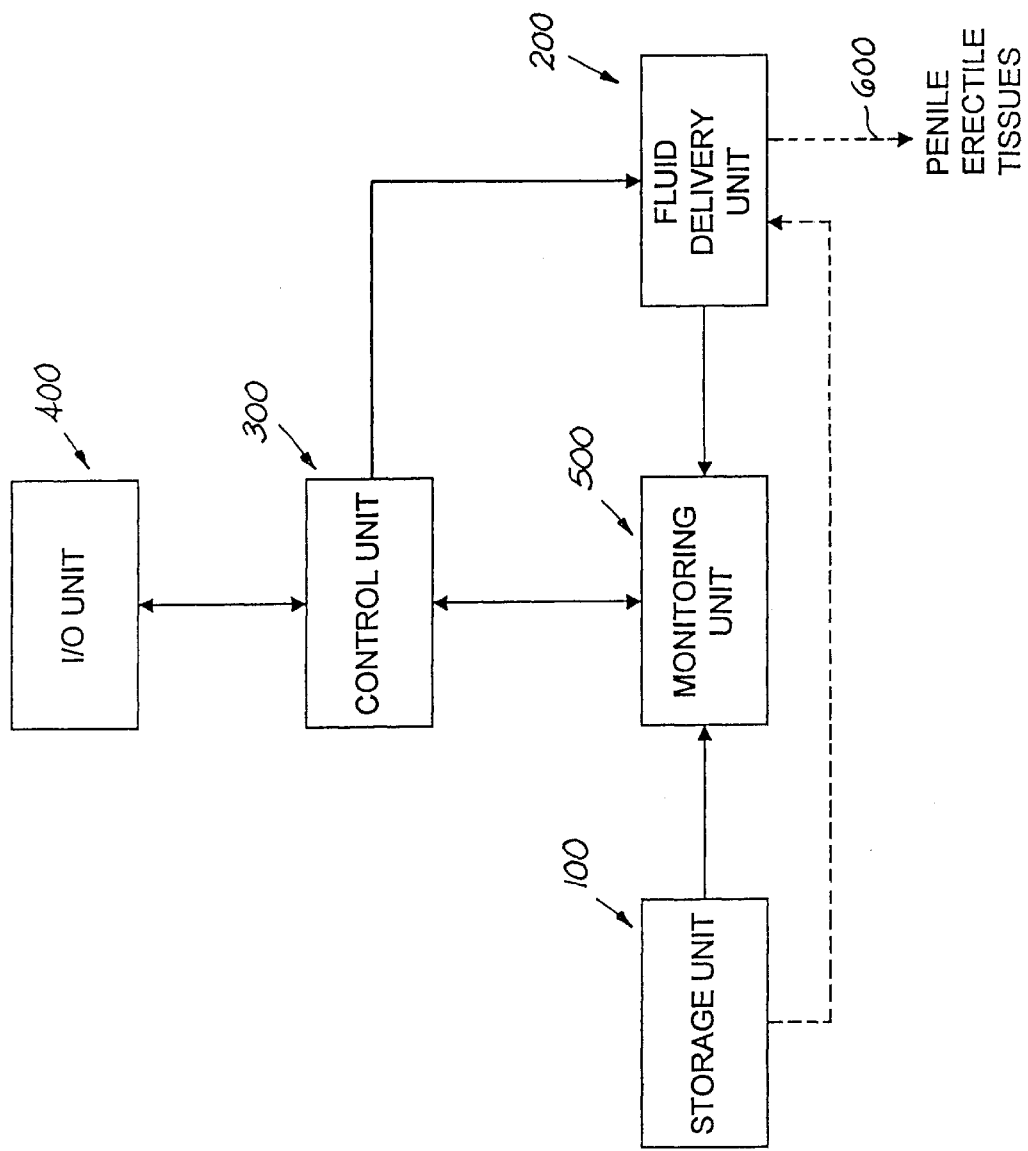

PENILE ERECTION ASSIST DEVICE AND METHOD

FIELD OF THE INVENTION

The present invention relates to a penile erection assist device and more particularly to an implantable penile erection device.

BACKGROUND OF THE INVENTION

Male patients suffering from impotence have been treated by several types of devices. Several prior patents have attempted to treat this condition by providing various types of mechanical prostheses placed on or implanted into the penis. For example, U.S. Pat. No. 5,509,891 to DeRidder proposes placing a condom-like sheath having retractable stiffeners embedded therein over the exterior of the penis. Disadvantageously, this type of device is visually apparent and therefore can be unappealing, and also may impair sensory feelings through the stiffener barrier.

Other types of penile prosthesis include surgically-positioned implantable prosthesis devices such as solid or inflatable units into the penis of patients. For example, U.S. Pat. No. 5,437,605 to Helmy et al. proposes implanting an elongatable remote controllable prosthetic device. The device is positioned in the penis and is operated to transfer fluid from one chamber to the other to elongate the prosthesis and cause an erection, and conversely permits withdrawal of the transferred fluid from the second chamber back to the first to effect a flaccid condition in the penis.

Examples of other implantable prostheses include U.S. Pat. No. 5,433,694 to Lim, U.S. Pat. No. 5,344,388 to Maxwell et al., U.S. Pat. No. 5,263,981 to Polyak et al., and U.S. Pat. No. 5,250,020 to Bley. Unfortunately, implanting mechanical prostheses almost always requires complicated surgery and can result in permanent destruction of intact erectile tissues. Thus, after implantation, the penile erectile tissues can suffer irreparable damage, and a once temporary condition can become chronic, thereby causing the patient to depend on the prosthesis for the rest of his life.

Even worse, after successful surgery, with many of the conventional mechanical prostheses, the penis may have to undergo additional surgery to replace the prosthesis, because inflatable prostheses tend to have unreliable performance and somewhat frequent mechanical malfunction. These problems are usually caused by high operating pressure required during the course of erection.

Drug therapy has recently been employed wherein patients can induce penile erection by injecting directly into their penis one or more locally acting vasodilating drugs such as prostaglandin E1, papaverine, or the like. However, injection of such drugs into a particularly sensitive organ using a needle almost always causes pain and, therefore, can inflict severe emotional distress onto the patient.

It is therefore an object of the invention to provide a non-intrusive, non-prosthesis penile erection device.

It is a further object of the invention to provide a penile erection device which reduces the pain associated with the delivery of the impotence treatment.

SUMMARY OF THE INVENTION

The penile erection assist device of the present invention treats impotent patients by providing physiologically active materials such as vasodilating drugs to the penile erectile tissues. The present invention overcomes the problems associated with previous devices and therapies by preferably implanting a major portion of the drug delivery system away from the situs to which drug is supplied. Thus, a high-precision drug delivery system can be advantageously implanted away from the sensitive reproductive organ, such as in the abdomen of a patient.

One aspect of the present invention is a penile erection assist device for treating patients with impotence. The device includes an implantable storage unit for storing physiologically active vasodilating materials including an inlet configured to be accessible from outside the patent's body without surgery and fluid delivery means operatively associated with the storage unit. The device also includes at least one thin sterile tubing hose in fluid communication with the storage unit and the fluid delivery means. The thin tubing has a proximal and distal end providing at least one delivery pathway, wherein the distal end is configured to be positioned adjacent penile erectile tissue for delivering the vasodilating fluids thereto.

An additional aspect of the present invention is a method for treating male impotence. The method includes positioning a section of thin sterile tubing internal to a patient such that a distal end is disposed at a location which is adjacent or contacting erectile penile tissue. The method also includes implanting a drug delivery device remote from the penis such that the drug delivery device is in fluid communication with the thin sterile tubing and inserting a predetermined dosage of a vasodilating material into the drug delivery device. The vasodilating drug is delivered to the penile erectile tissue to stimulate an erection therein.

A further benefit of the present invention is the minimum erectile tissue disruption created by the delivery system which is employed to deliver the drug. For example, by extending one end of the thin sterile tubing into the proximal portion of the erectile tissues and connecting the other end of the tubing to the pumping mechanism of the drug delivery system, the desired vasodilating material can be effectively supplied to the penile erectile tissues, while minimizing the damage to such tissues. Accordingly, the penile erection assist device of the present invention advantageously preserves the intact function of the penile erectile tissues by minimally intruding into those tissues; the device is applicable to patients with impotence of various etiologic origins, and is applicable acutely or permanently, according to the needs of the patients.

The penile erection assist device of the present invention is implanted inside the patient's body but preferably includes a control and monitoring unit which is accessible for user interface and adjustments. Dosage of vasodilating drug is typically pre-determined by medical personnel depending on the severity and/or characteristics of the patient's impotence. Additionally and advantageously, the present invention includes a user interface I/O unit which communicates with the implanted portion. Thus, dosage can be conveniently adjusted depending on the patient's condition.

Also, the patient with the implanted penile erection assist device of the present invention can obtain erection by entering a command to the control unit through the user interface or I/O unit. Responsive to the command, the control unit delivers a specified amount of vasodilating drug to the penile erectile tissues according to a preferably preset or adjusted dosage of the drug. The user interface unit monitors and displays to the user the control results and other operational characteristics of the penile erection assist device, such as the availability of the vasodilating drug in terms of the amount, the number of injections, any blockages, and the like.

BRIEF DESCRIPTION OF THE DRAWINGS

FIG. 1 is a block diagram schematically illustrating a penile erection assist device of the present invention.

DETAILED DESCRIPTION OF THE PREFERRED EMBODIMENTS

Figure 2A:
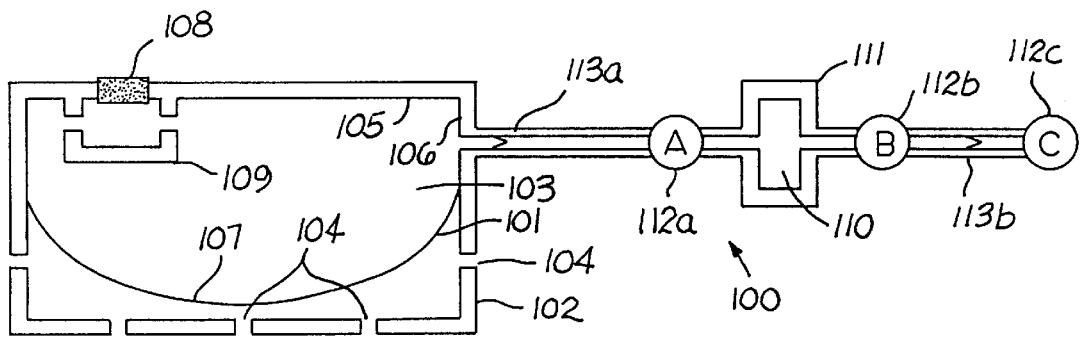
FIG. 2(A) is a cross-sectional view of a storage unit of the penile erection assist device of the present invention.

The present invention will now be described more particularly hereinafter with reference to the accompanying drawings, in which present embodiments of the invention are shown. The invention can, however, be embodied in many different forms and should not be limited to the embodiments set forth herein; rather, these embodiments are provided so that this disclosure will be thorough and complete and will fully convey the scope of the present invention to those skilled in this art.

Referring now to the drawings, FIG. 1 is a block diagram schematically illustrating a penile erection assist device of the present invention. Generally described, a storage unit 100 stores physiologically active vasodilating drugs in a storage chamber defined therein. The storage unit is implanted in the body of a patient, and is preferably positioned remote from the sensitive penile tissue. Thin sterile tubing 600 is attached to the storage unit and disposed in the patient to transport the drug from the remotely positioned storage unit to the penile erectile tissue. A fluid delivery unit, such as a pumping unit 200, pumps the prescribed drug dosage from the implanted storage unit 100 through implanted sterile thin tubing 600 and preferably into the proximal end of penile erectile tissues in accordance with a command signal from a user. It is preferred that a control unit 300 control the delivery of a vasodilating drug based on information from the input/output ("I/O") or user interface unit 400 and the monitoring unit 500. For example, the user interface I/O unit 400 supplies various input commands, such as drug dosage information, to the control unit 300. The control unit or monitoring unit 300, 500, respectively, responds to the input and also monitors certain operational characteristics of the storage unit 100 and the fluid delivery unit 200.

Accordingly, the control unit 300 of the penile erection assist device controls the fluid delivery unit 200 which supplies (upon command) vasodilating materials to the penile erectile tissues. Examples of vasodilating materials which can be employed in the device include, but are not limited to, conventionally locally-acting vasodilating drugs such as prostaglandin El, papaverine, or the like. Additionally, hormones, neurotransmitters, and derivatives thereof can also be used as long as they can induce penile erection when they are provided near or into the penile erectile tissue or into the bloodstream fed to the penile erectile tissue.

Preferably, the monitoring unit 500 provides information regarding the amount of remaining drug, power reserve, and various other operational characteristics of the storage unit or fluid delivery unit (for example, a pumping unit) 200 based on information detected in various locations in the device or fluid pathways, such as the pressure in the storage chamber storage unit 100 and the fluid delivery unit 200. Although the control unit 300 and the monitoring unit 500 have been described as two separate units, the functions could be easily combined into one unit and perform equivalently. Accordingly, in order to more clearly describe the invention, the term "control unit" will be used hereinafter to describe a control unit which is inclusive of a separable monitor unit, i.e., a unit which can direct the function of the device as well as monitor and maintain certain operational parameters which are deemed desirable. Additionally, the fluid delivery unit as used herein can be any conventional fluid delivery means, such as, but not limited to, pressure or displacement or other type of fluid transfer devices, such as rotational, impeller, or peristaltic pumps, and the like.

FIGS. 2(A) and (B) show two exemplary embodiments of a storage unit 100. In FIG. 2(A), a diaphragm container 101 is installed in the housing 102 to contact and preferably seal against the inner top 105 and inner side walls 106 of the storage housing 102 to define a storage chamber. Preferably, the lower portion of the diaphragm container 101 is not fixed either to the top 105 or to the side walls 106 of the storage case 102. Accordingly, the diaphragm container 101 is substantially flexible and can maintain relatively constant inner pressure during operation or refilling of the device through contraction and expansion of the lower portion of the diaphragm container 101. On one part of the storage case 102, a septum entry port 108 is provided through which vasodilating drugs can be replenished or refilled into the storage chamber. It is preferred that a hypodermic syringe type device be employed to allow percutaneous replenishing, as needed, of a desired amount of fluid/drugs into the septum 108 of an implanted diaphragm container; advantageously, this technique does not require surgical access. It is also preferred that a needle advancement stop, such as a solid plate 109, be positioned underneath the septum 108 and inside the diaphragm container 101 in order to prevent excessive insertion of a needle and any resulting damage to the diaphragm container 101 during refilling the storage unit 100 with vasodilating drug.

A filter 111 charged with physically and/or chemically active substances 110 may be installed at the outlet of the diaphragm container 101 in order to remove foreign material that may be present in the drug. It is preferred that, at the proximal and distal ends of the filter 111, one-way valves 113a, 113b are provided to prevent retrograde flow of filtrates. It is also preferred that, at both ends of the filter 111, multiple conventional air-proof or self-sealing connectors 112a, 112b be incorporated in order to facilitate air-tight modular replacement of tubing or the like; this is done in the event that one part or module would need to be replaced due to blood clogging or mechanical or physical damage without necessitating the removal of the entire implanted unit. Although illustrated on either side of a filter, it will be appreciated that such connectors could be provided at any number of positions.

Figure 2B:
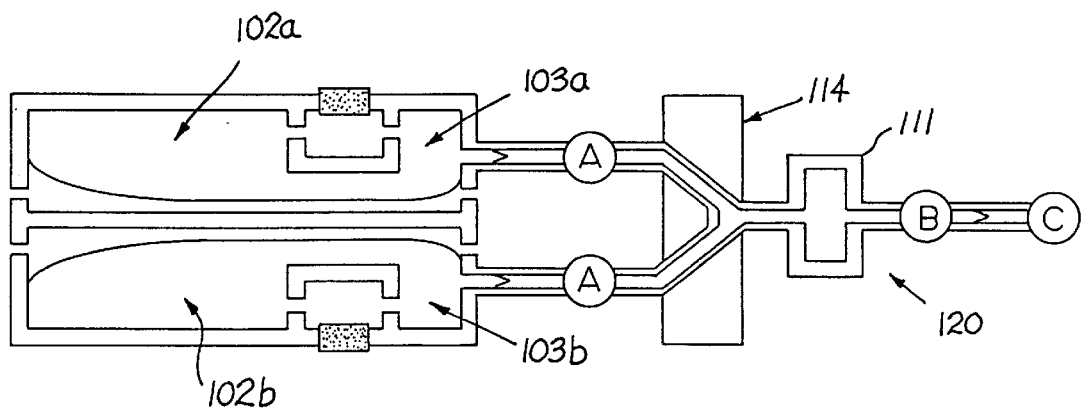
FIG. 2(B) is a cross-sectional view of an alternative embodiment of a storage unit of the present invention.

FIG. 2(B) shows an alternative embodiment of a storage unit 120 having multiple storage chambers 102a, 102b with multiple diaphragm containers 103a, 103b. As illustrated, the multiple diaphragm containers 103a, 103b exit from the storage unit to initially create two fluid pathways which are funneled into a single filter 111, such as by way of a three-way valve 114. The storage unit 120 in FIG. 2(B) operates the same way as the storage unit 100 shown in FIG. 2(A) as described hereinabove. However, the storage unit in FIG. 2(B) 120 has an advantageous redundancy and, thus, is capable of supplying vasodilating drug even if one subunit malfunctions.

Although not shown in FIGS. 2(A) and 2(B), the storage unit and the pumping unit, can be combined into a single integral unit (for example, by using a large syringe-type pump wherein the cylinder of the syringe pump stores vasodilating drug). Other examples include the embodiments shown in FIG. 3(C) and FIG. 4(A)–(C), which could also be configured to function as a combined storage-pumping unit. Such an integral configuration advantageously eliminates the need for a separate storage and pumping unit.

Various embodiments of the fluid delivery unit including various pumping units 200 which pump vasodilating drug to the penile erectile tissues are described in FIGS. 3 and 4. Generally described, the fluid delivery unit includes a pumping unit 200 comprising three functional modules: a power-generating module 201, a power supply module 202, and a conversion module 210, 220, 230, 240, 250, 260 which converts the rotational motion of the power generating module 201 into a displacement motion through which vasodilating drug is discharged to the penile erectile tissues. As illustrated, it is preferred that, along the passages or tubing 207a, 207b connecting the fluid delivery unit 200, one-way valves 208a, 208b and conventional air proof or self-sealing connectors 209a, 209b be incorporated into the fluid delivery pathway. In the Figures, the circled capital letters A, B, C, and D correspond to self-sealing interconnections between modules; the interconnections being disposed along an exemplary flow path at serially aligned positions. For example, in FIG. 3, a connector 209a (indicated as C) connects to a corresponding connector 112c in FIGS. 2(A) and 2(B), with C indicating an input and D an output fluid flow direction as indicated by the arrows in FIGS. 3 and 4.

Figure 3A:
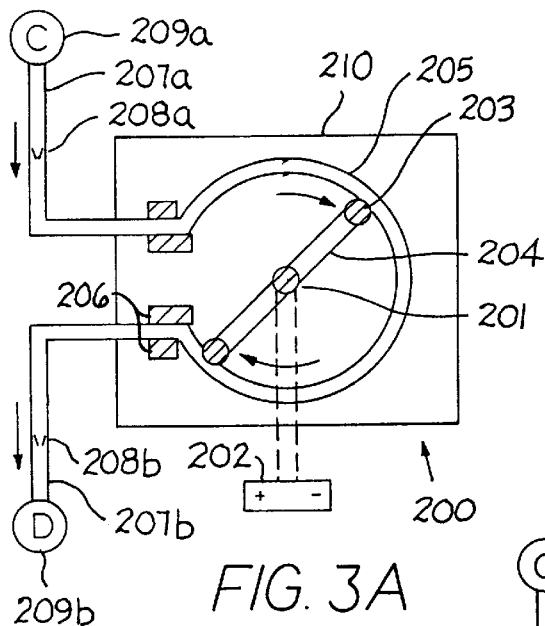
FIG. 3(A) is a cross-sectional view of a fluid delivery means of a penile erection assist device of the present invention.
Figure 3B:
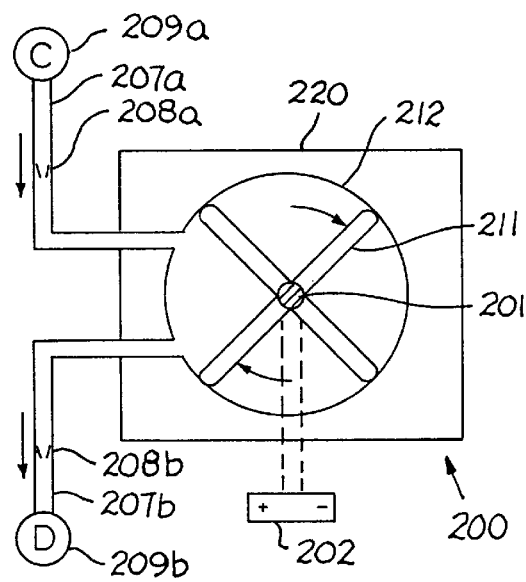
FIG. 3(B) is a cross-sectional view of an alternative embodiment of a fluid delivery unit of the present invention.
Figure 3C:
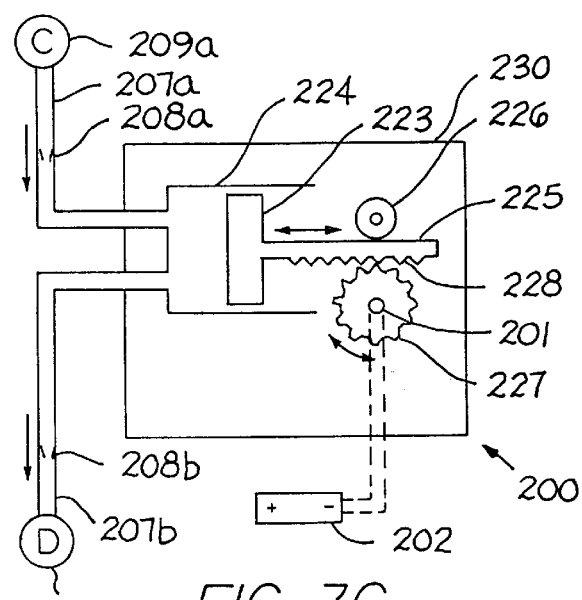
FIG. 3(C) is a cross-sectional view of yet another alternative embodiment of a fluid delivery unit of the present invention.
Figure 4A:
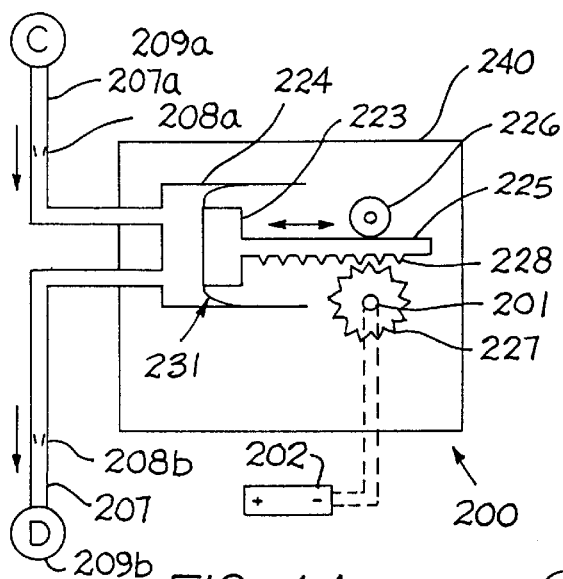
FIG. 4(A) is a cross-sectional view of another alternative embodiment of a fluid delivery unit of the present invention.
Figure 4B:
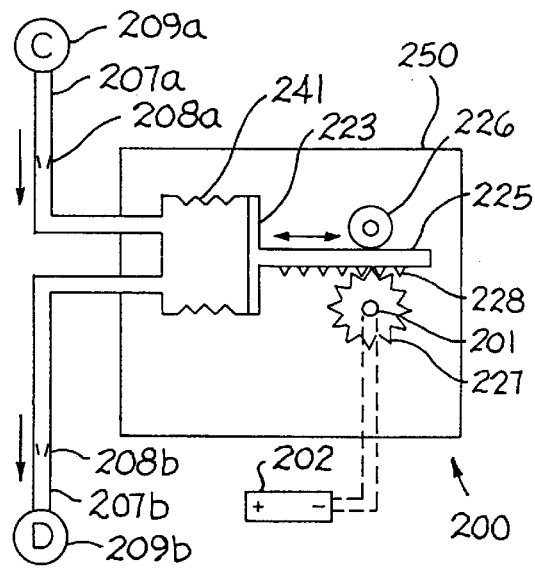
FIG. 4(B) is a cross-sectional view of another alternative embodiment of a fluid delivery unit of the present invention.
Figure 4C:
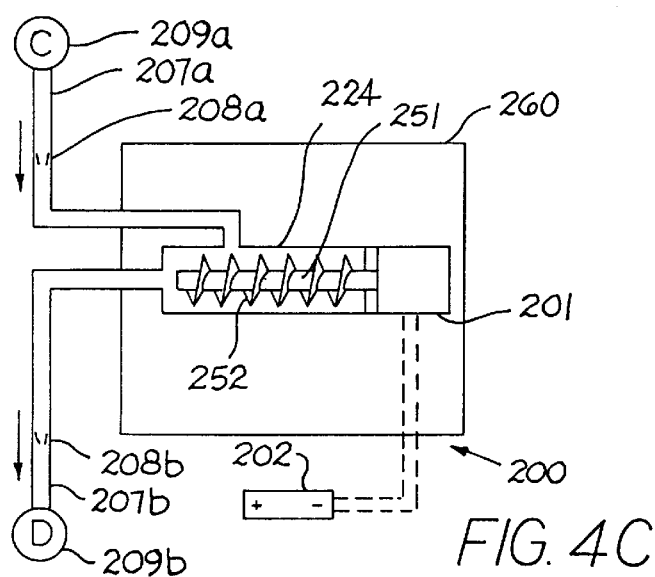
FIG. 4(C) is a cross-sectional view of yet another alternative embodiment of a fluid delivery unit of the present invention.

The fluid delivery unit 200 can have various embodiments according to the characteristics of the conversion modules, several exemplary embodiments of which are shown in FIGS. 3 and 4. For the ease of reference, in those figures, the power-generating module 201 and the power supply module 202 are represented by a DC motor and a DC battery, respectively. FIG. 3(A) represents a peristaltic conversion module 210 comprising a roller 203, a rotating shaft 204, tubing 205, and a tubing support 206. FIG. 3(B) illustrates an impeller-type conversion module 220, comprising an impeller 211, and a cylindrical impeller housing 212; and FIG. 3(C) illustrates a syringe-type conversion module 230, comprising a piston 223, a cylinder 224, a piston axle 225, an axle support 226, a gear 227, and a pinion 228. FIG. 4(A) illustrates a diaphragmatic conversion module 240, comprising a piston 223, a cylinder 224, and a resilient flexible diaphragm 231. FIG. 4(B) illustrates a bellows-type conversion module 250, comprising a piston 223 and a cylinder with bellow around the circumference thereof 241; and FIG. 4(C) illustrates a screw pump-type conversion module 260, comprising a cylinder 224, an axle 251, and a screw-shaped impeller 252.

Figure 5A:
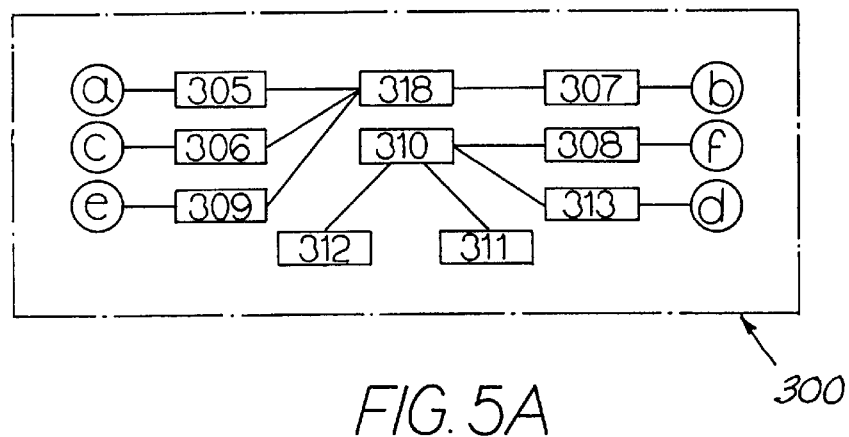
FIG. 5(A) is a schematic diagram of a control unit of the penile erection assist device of the present invention, wherein the control unit controls the storage unit and the fluid delivery unit of a penile erection assist device of the present invention.
Figure 5B:
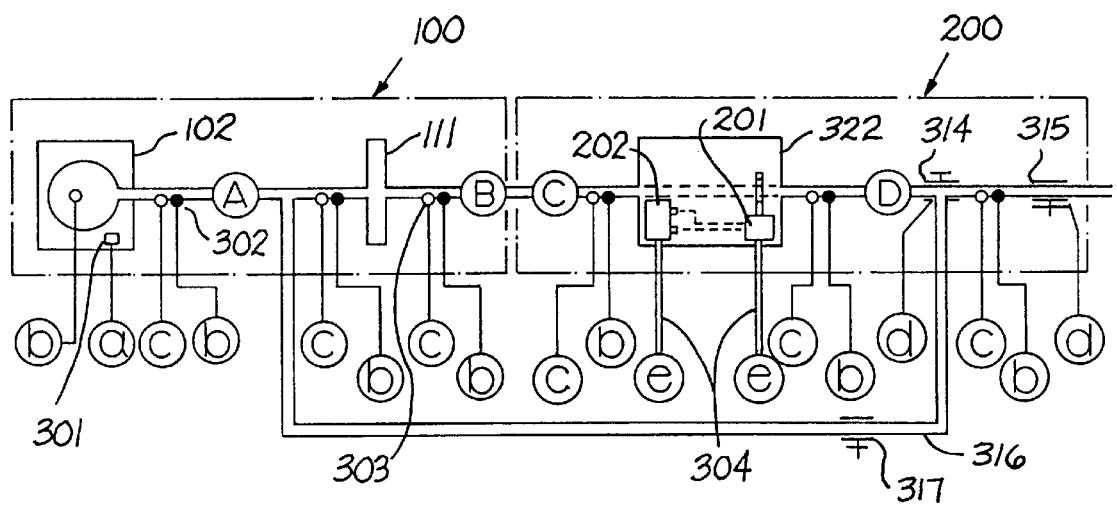
FIG. 5(B) is a schematic diagram of a storage unit and fluid delivery unit of the present invention.
Figure 6A:
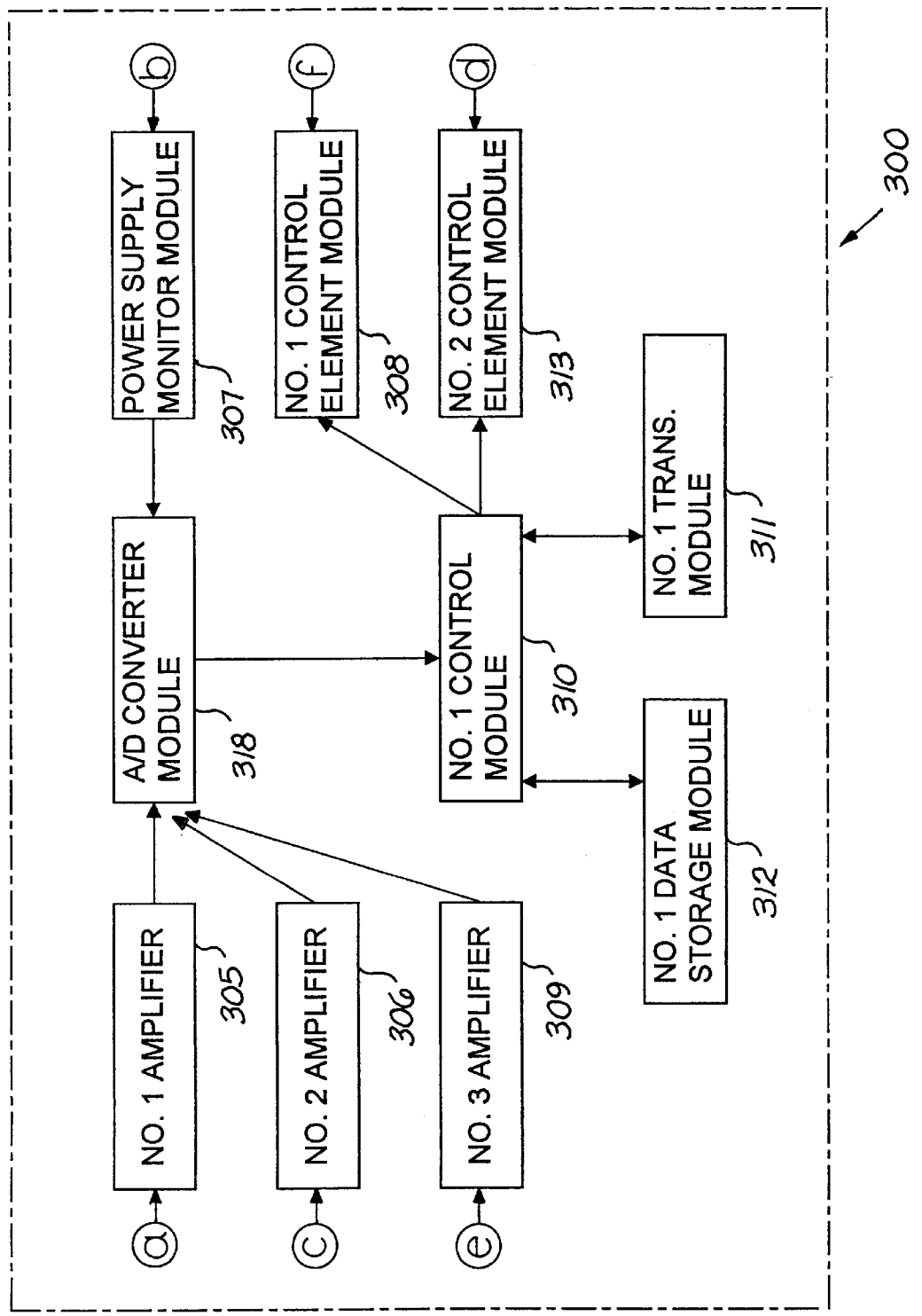
FIG. 6(A) is a schematic diagram of an alternative control unit of the penile erection assist device of the present invention.
Figure 6B:
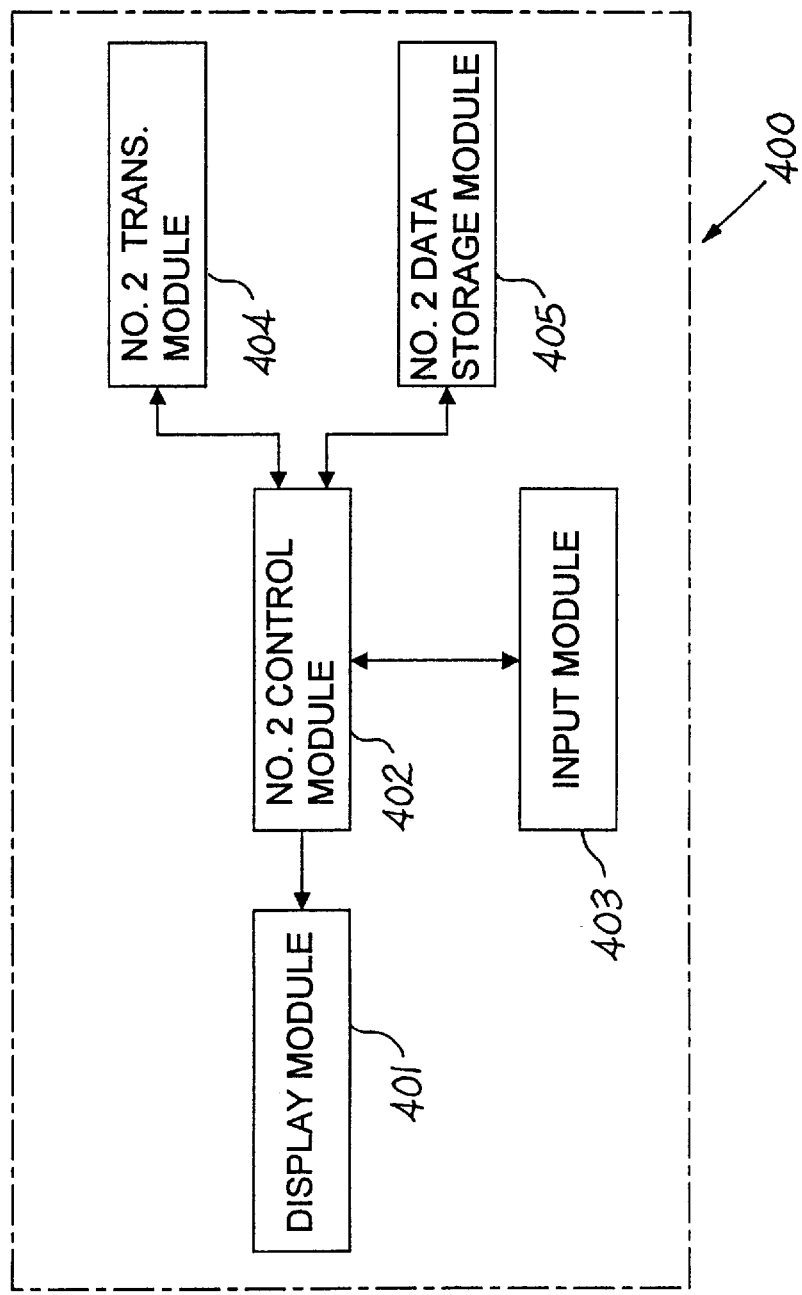
FIG. 6(B) is a schematic diagram of a user interface or I/O unit of the present invention.
Figure 7:
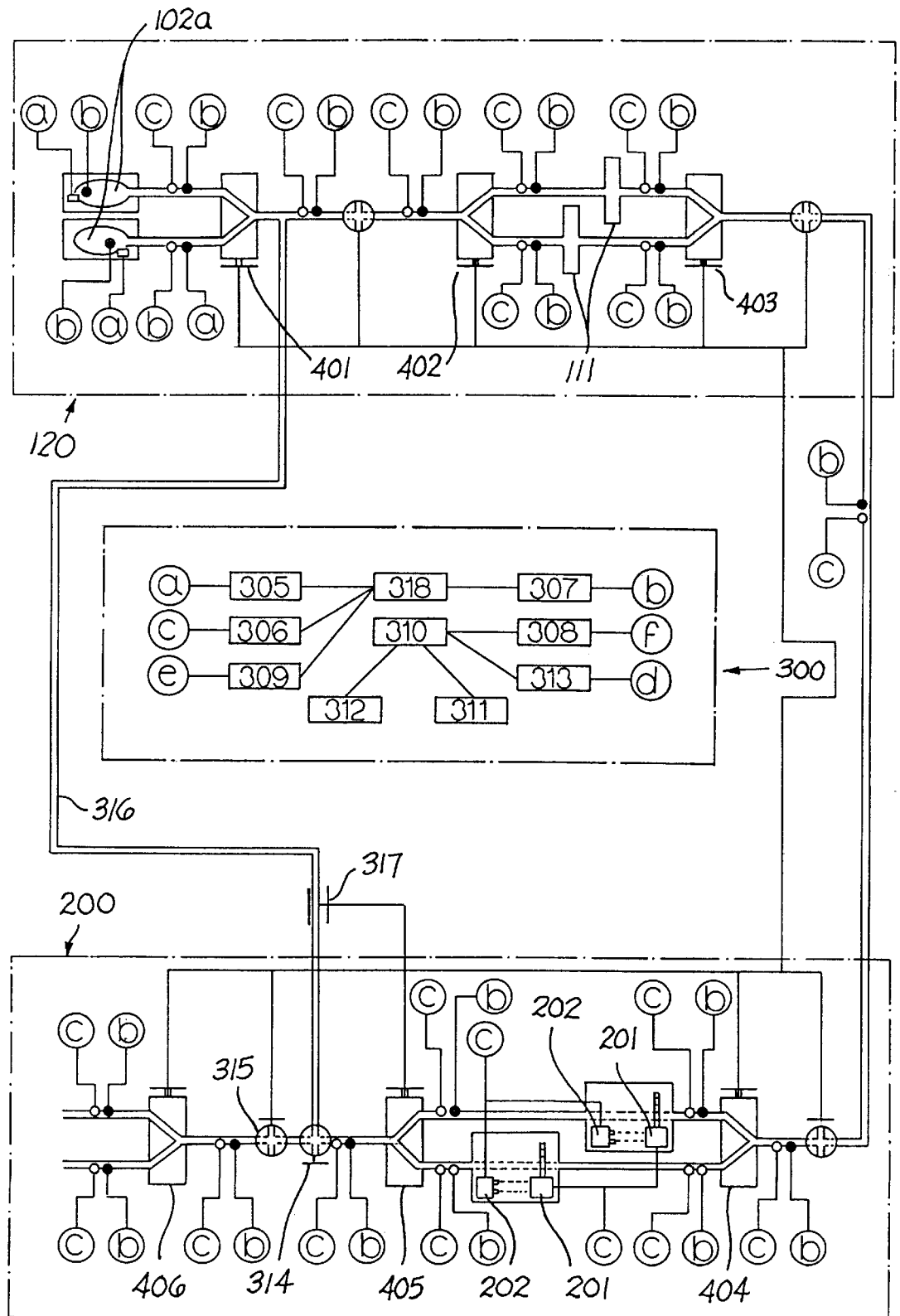
FIG. 7 is a schematic diagram of a control unit, a fluid delivery unit, and a storage unit of the penile erection assist device of the present invention.

In operation, a control unit 300 controls the storage unit 100 and the fluid delivery unit 200. FIG. 5(A) shows a block diagram of a control unit 300 which controls the functions of the penile erection assist device of the present invention. As schematically illustrated in FIG. 5(B), a control unit controls a single storage unit 100 and a fluid delivery unit having a single pumping unit 200. FIG. 6 illustrates one embodiment of a control unit and corresponding user interface or I/O unit 400. In particular, FIG. 6(A) shows a diagram of the control unit in FIG. 5(A). FIG. 7 is a schematic diagram of the control unit 300 which controls multiple storage units 100 and a fluid delivery unit having multiple pumping units 200. As illustrated, notwithstanding the number of units to be controlled, the control unit in FIG. 7 is substantially the same as the one in FIG. 6(A) or FIG. 5(A). Accordingly, for ease of discussion, the following description will be centered upon the control units shown in FIGS. 5 and 6, but it will be appreciated by those of skill in the art that the description is illustrative of devices including multiple pumps or storage chambers, and more than one fluid delivery pathway.

In FIG. 5(B), conventional displacement sensors 301 and/or pressure sensors 302 are provided in the storage unit 100 to detect and monitor the location and inner pressure of the diaphragm container 101, the pressure of the gap between the container and the storage housing, and the pressure along the fluid pathway. Conventional pressure sensors 302 and/or flow meters 303 may also be provided at the proximal and distal ends of each of any additional elements such as connectors, filters, and one-way valves, in order to detect and monitor pressures thereof and flow rates therethrough. In addition, conventional voltage and/or current meters 304 may be provided in the fluid delivery unit 200 in order to monitor voltage, current, and/or power thereof. It is preferred that the output signals of any sensors employed in the device are sent to at least one amplifier, which are preferably positioned in the control unit. In the Figures, exemplary output or input signals are represented as (a) (displacement signal detected by displacement sensor 301), (b) (pressure signal detected by pressure sensor 302), (c) (flow signal detected by flow meter 303), (e) (voltage or current or power detected by meters of same type 304), (d) (control signal manipulating a fluid delivery pathway 314, 315), and (f) (auxiliary control signal).

As illustrated, the detected signals are sent to four amplifiers 305, 306, 307, 309, amplified thereby, and then fed to the No. 1 control module 310. After receiving the output signals from the displacement sensors, pressure sensors, flow meters, and voltage and/or current meters, the No. 1 control module, responsive to the signals, determines any necessary adjustments or warnings, performs control based thereon, and the resulting operational characteristics are preferably sent to the user interface 400 (or medical and/or control personnel) via the I/O transmission module 311. The signals measured by the sensors and those determined by the control module 310 can be stored, if necessary , by the No. 1 Data storage module 312.

In operation, the No. 1 control module 310 determines whether individual sensors are working properly by checking their output signals. In case one or more sensors malfunction (as indicated by the detection of open-circuit or out-of-range signals), the No. 1 control module can turn on an alarm by sending a special signal to an external I/O or user interface unit 400 via the No. 1 transmission module 311. The signals are then received by the user interface I/O unit 400, such as by the No. 2 transmission module 404 shown in FIG. 6(B). The user interface can preferably display abnormal operation of the sensors through a display module 401. The operational signals may also be stored, as desired, such as by the No. 2 data storage module 405.

When all sensors are working properly, the No. 1 control module 310 estimates the amount of drug remaining in the storage unit based on the output signals of pressure 302 and/or displacement sensors 301. The control unit, typically through the No. 1 control module 310, then compares the amount of remaining drug with the minimum set-point of the amount of drug. If the remaining amount is smaller than minimum set-point, the control unit, again typically through the No. 1 control unit 310, sends a signal to alert or alarm the user (preferably either through a visual or auditory message or signal transmitted through the user interface 400) to refill the storage unit with a prescribed amount of vasodilating drug.

The control unit 300, typically through the No. 1 control module 310, preferably also compares the voltage, current, and/or power of the power supply module 202 associated with the fluid delivery unit 200 with corresponding minimum set-points. If the control unit determines that one or more of voltage, current, and/or power are smaller than the corresponding minimum set-points, the control unit 300, via No. 1 control module 310, sends a signal to alarm the user to recharge the power supply module 202, and maintains the system at stand-by position until the power supply module 202 is recharged.

The control unit 300 also checks whether a prescribed dosage of vasodilating drug is preset. If the dosage is preset without adjustment options or if a new dosage signal is sent from the user interface 400 and received by the control unit 300, such as through the No. 1 transmission module 311, the No. 1 control module 310 sends a ready signal to the user via the user interface 400 and waits for the operation command (i.e., start), final approval, or further adjustment by the user or physician.

Preferably, the ready signal is received by the No. 2 transmission module 404 of the user interface I/O unit 400, and is displayed by the display module 401, which is operatively controlled by the control unit 300, typically through the No. 2 control module 402. The user can approve or change the dosage of the drug using the input module 403, and the final confirmed or adjusted dosage is communicated to the No. 1 control module 310 via the No. 1 and No. 2 transmission modules 311, 404. Then, the No. 1 control module 310 controls the operating characteristics of the fluid delivery unit 200 and sends the signal to the user that confirmation or adjustment is ready.

The No. 1 control module 310 determines whether the activation or confirmation signal for discharging vasodilating drug is received from the user. If the signal is not received, the No. 1 control module 310 stops the procedure, repeats the above procedure as necessary, or goes into a power-saving standby mode. However, if the control unit receives a signal, it then determines whether the signal indicates to initiate a test-run for the purpose of calibration or to inject vasodilating drug through a fluid delivery pathway to the penile erectile tissues. As illustrated in FIG. 5(B), if the user commands the test-run, the control unit, typically through the No. 1 control module 310, controls the No. 2 control element 313 to enter into the test-mode. The control unit engages a recirculation pathway 316 by closing the distal fluid delivery pathway via a control valve 315 and opening the recirculation pathway by the valve 314. Then the control unit, such as through the No. 1 control module 310, controls the fluid delivery unit 200 such that a specified test dosage of vasodilating drug is recirculated from the storage unit 100 through the recirculation fluid passage, and then back to the storage unit 100. Alternatively, when the user commands the normal injection of vasodilating drug, the control unit 300, opens the distal fluid pathway via a control valve 315, closes the recirculation pathway by a valve 314, and delivers vasodilating drug from the storage unit 100 to the penile erectile tissues.

FIG. 7 shows another embodiment of the penile erection assist device of the present invention, wherein elements such as storage chambers 102a, filters 111, motors 201, batteries 202 and the like are provided in a plurality of positions within the device. As illustrated, the device also employs final control valves 401, 402, 403, 404, 405, 406. Accordingly, the control unit 300 can direct vasodilating materials and drugs or vasodilating-inducing substances in a desired manipulatable fluid pathway by manipulating the control valves and by securing an open fluid pathway around certain elements; thereby insuring operability even when one or two elements of the device become inoperable or malfunctions. Although not shown in the figure, multiple recirculation pathways 316 and control unit 300 or other components can also be redundantly provided to assure reliable operation thereby.

Figure 8:
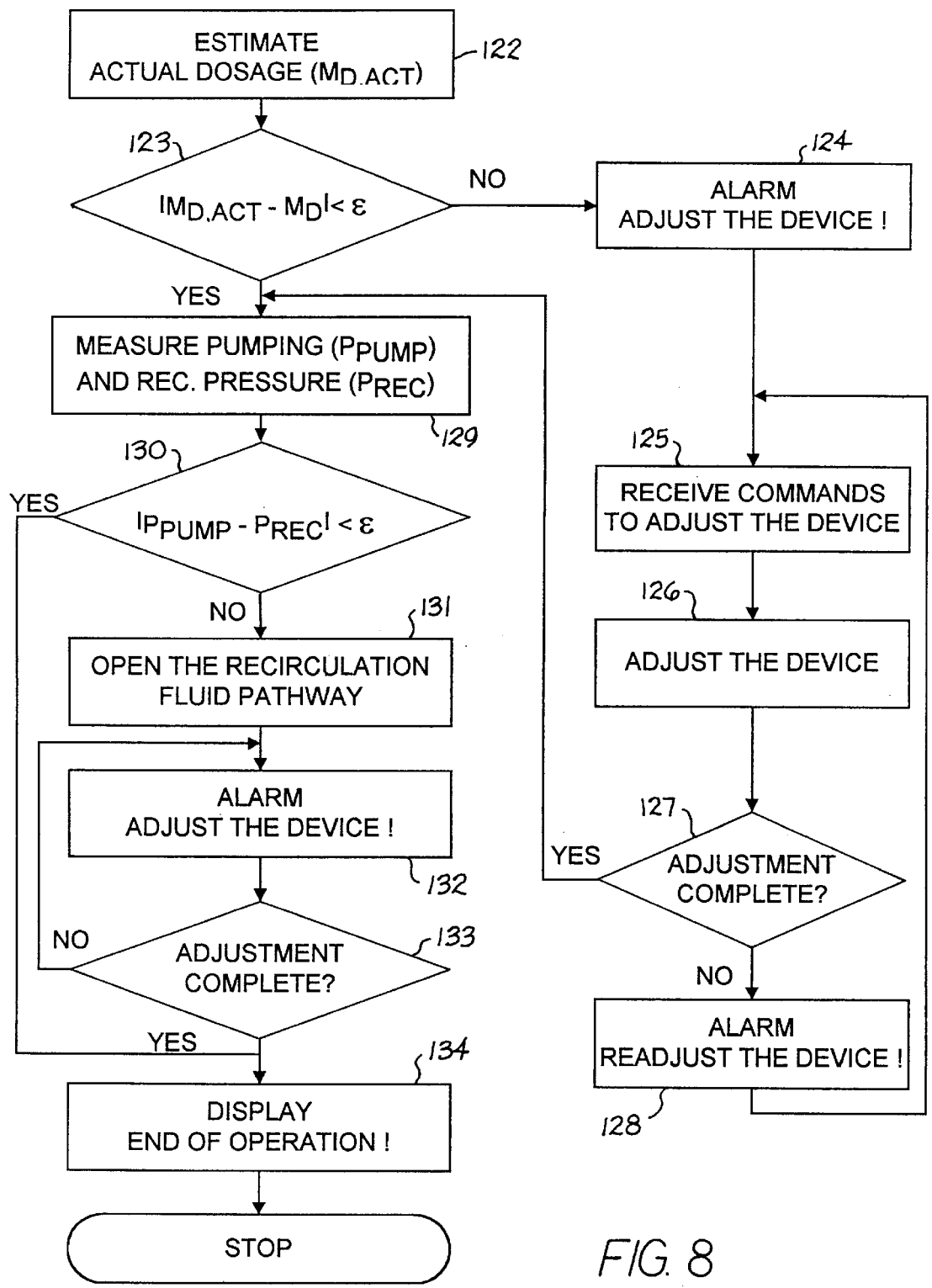
FIG. 8 is a flow chart illustrating exemplary operational steps of a control unit of the penile erection assist device of the present invention.

As illustrated by the flow chart in FIG. 8, it is preferred that, during a test run or after the completion of the delivery of the vasodilating drug, the control unit, such as through the No. 1 control module 310, receives signals from the displacement or pressure sensors and/or the flow meters (a, b, c). The control unit then determines the amount of actual dosage (within certain tolerances) of the drug pumped to the recirculation pathway or to the penile erectile tissues, and then compares the actual dosage with the preset or prescribed value, illustrated by blocks 122, 123 in FIG. 8. If the calculated or actual dosage falls within the tolerance range, then the next step is performed 129. Otherwise, the control unit communicates the status or alarms the user regarding the discrepancy between the actual and desired or prescribed dosages. The device then preferably requires the user to calibrate and/or adjust the device using the input module 403 of the user interface I/O unit 400. It is also preferred that, until the problem as to the dosage discrepancy is properly solved or intentionally accepted, the control unit 300, via No. 1 control module 310, performs other commands, while preferably maintaining the alarm signal until calibration and/or adjustment is performed 122–128.

It is also preferred, as illustrated by blocks 129–134, that once the determined ($M_D$) and actual ($M_{Dact}$) dosage is within the tolerance range, the control unit, such as via the No. 1 control module 310, then compares the output pressures from the fluid delivery unit or pathway with that from the recirculation pathway (i.e., pumping delivery pressure to pumping recirculation pressure). If the difference between the two pressures exceeds the tolerance range block 130, the control unit, such as via the No. 1 control module 310, opens a recirculation pathway 131 via a valve 314 and sends an alarm signal 132 for adjustment. The operational steps are illustrated by blocks 129–133.

A potential problem associated with the implanted device is that the distal tip of the tubing, which is in constant contact with the penile erectile tissues, may become clogged for various reasons, such as due to blood clotting. Such clotting can be prevented by providing control valves adjacent the distal tip of the tubing. A suitable control valve, various types being well known to those of skill in the art, would preferably open only during the discharge of the vasodilating drug at the direction of the control unit, or a component therein such as by the No. 1 control module 310 and the No. 1 control element module 308.

The penile erection assist device in treating impotent patients can be provided not only according to the above exemplary embodiments, but also by modifications without materially departing from the novel teachings and advantages of this invention. For example, the drug delivery system of this invention may comprise multiple storage units 100 such that, even if the main storing unit malfunctions, the system can supply vasodilating drug to the penile erectile tissues by switching the source of the drug to the secondary storing unit. The discharging volume of the drug can also be controlled with a greater precision by controlling the supply voltage and/or current to the power generating module of the pumping unit 200, by controlling the displacement of the conversion module of the pumping unit 200, or by installing an additional pressure reservoir along the fluid pathway. In addition, a secondary pumping unit can also be provided which discharges vasodilating drug to the penile erectile tissues only when the primary pumping unit fills the prime chamber of the secondary pumping unit with the prescribed volume of the drug.

The penile erection assist device of this invention has substantial advantages in treating patients with impotence, because a major portion of the device can be implanted inside the patient's body remote from the sensitive, fragile, penile tissue; this device and method can also advantageously minimize the destruction of the penile erectile tissues of the patient, and therefore, may be used either acutely or permanently.

Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses are intended to cover the structures described herein as performing the recited function and not only structural equivalents but also equivalent structures. The foregoing is illustrative of the present invention and is not to be construed as limiting thereof. The invention is defined by the following claims, with equivalents of the claims to be included therein.

That which is claimed is:

1. A method for treating male impotence, comprising the steps of:

positioning a section of thin sterile tubing within a patient such that a distal end is disposed at a location which is adjacent or contacting erectile penile tissue;

implanting a drug delivery device remote from the penis of a patient such that the drug delivery device is in fluid communication with the thin sterile tubing defining a first delivery pathway therebetween;

inserting a predetermined dosage of a vasodilating material into said drug delivery device; and delivering the predetermined vasodilating material through the thin tubing to the penile erectile tissue to stimulate an erection therein.

2. A method according to claim 1, further comprising the step of:

positioning said drug delivery device in the abdomen of a patient.

3. A method according to claim 1, further comprising the steps of:

activating operation of the delivery of the vasodilating material in the drug delivery device in response to a remote external signal; and controlling the amount of vasodilating material delivered to erectile penile tissue based on a predetermined selection; and alerting the user when the amount of drug in the drug delivery device is less than a preset amount.

4. A method according to claim 1, further comprising the step of:

testing operational function of the drug delivery device via a recirculating test dosage pathway different from a fluid delivery pathway.

5. A method according to claim 1 further comprising the step of:

detecting operating deficiencies at predetermined sensor locations and providing operational status information thereby to a user interface accessible to a patient.

6. A method according to claim 1 further comprising the step of:

replenishing vasodilating material in the implanted device by receiving a syringe into a drug entry port positioned in said implantable device.

7. A method for treating male impotence, comprising the steps of:

implanting a drug delivery device remote from the penis of a patient;

inserting a predetermined amount of vasodilating material into said drug delivery device;

forming at least one drug delivery pathway having a proximal end and a distal end, said pathway being disposed internal to the patient such that a proximal end of said pathway is in fluid communication with said fluid delivery device, and a distal end is disposed adjacent erectile penile tissue, wherein said drug delivery device delivers vasodilating material to erectile penile tisse to dilate penile vasculature thereby to result in penile erection.

8. A method according to claim 7, further comprising the step of:

providing at least one of displacement, pressure, flow, and voltage sensors to monitor operational parameters of said drug delivery device.

9. A method according to claim 8, further comprising the step of:

adjusting predetermined operational parameters of said implanted delivery device by a control unit located outside the body responsive to operating deficiencies detected by said sensors.

10. A method according to claim 7, further comprising the steps of:

forming a plurality of serially connecting modular subunits of said drug delivery device by positioning valves in predetermined locations along said fluid delivery pathway to allow manipulation of said fluid pathway and to allow for modular replacement of malfunctioning components.

11. A penile erection assist device for treating patients with impotence, comprising:

an implantable storage unit for storing physiologically active vasodilating material, said storage unit including an inlet configured to be accessible from outside the patient's body without surgery, said storage unit comprising a housing and a flexible diaphragm container sealed to and positioned within said housing to define a storage chamber for a vasodilating material;

fluid delivery means operatively associated with said storage unit;

at least one implantable thin sterile tubing hose in fluid communication with said storage unit and said fluid delivery means and having a proximal and distal end providing at least one delivery pathway, wherein said distal end is configured to be positioned adjacent penile erection tissue for delivering the vasodilating material thereto;

a control unit operatively associated with said fluid delivery means for controlling the delivery of said vasodilating material stored in said storage unit, said control unit including a plurality of sensors for detecting and monitoring operational parameters of said device, wherein at least one of said plurality of sensors is operatively associated with said fluid delivery means and at least one of said plurality of sensors is operatively associated with said storage unit; said plurality of sensors including a plurality of pressure sensors which detect a plurality of operating parameters, wherein a first pressure sensor is positioned in said housing to detect the pressure of the drug in said diaphragm container, thereby indicating the amount of drug available therein, wherein a second pressure sensor is positioned adjacent the proximal end of said thin tubing hose to detect and thereby monitor the pressure of the drug as it is discharged from said storage container, wherein a third pressure sensor is positioned to detect the pressure of the drug taken into said fluid delivery means, and wherein a fourth pressure sensor is positioned to detect the pressure of the drug discharge from said distal end of said tubing and thereby delivered to the penile erectile tissues; and a user interface unit positioned remote from said storage unit operatively associated with said control unit and accessible by a patient to allow adjustment or activation of said device and for providing input/output communications therebetween.

12. A penile erection assist device according to claim 11, wherein said control unit determines the amount of vasodilating material remaining in said storage unit responsive to one of pressure and displacement of said vasodilating material inside said diaphragm container and then displays the results on said interface unit.

13. A penile erection assist device according to claim 11, wherein said control unit generates a warning when the amount of said vasodilating material is below a predetermined level.

14. A penile erection assist device according to claim 11, wherein said control unit monitors and detects discrepancies between a predetermined dosage level of said vasodilating material and the amount delivered to the penile erectile tissues and communicates the information to the patient.

15. A penile erection assist device according to claim 11, wherein said storage unit comprises:

a septum entry port for receiving a needle to deliver a predetermined dosage of said vasodilating material into said diaphragm container; and a needle advancement stop positioned adjacent said septum entry port configured to allow delivery of a fluid from the needle into said housing and diaphragm and to prevent the needle from advancing beyond said stop to protect said diaphragm container from damage due to excess needle penetration.

16. A penile erection assist device according to claim 11, wherein said fluid delivery means and said storage unit are configured to define an integral unit.

17. A penile erection assist device according to claim 16, wherein said integral unit comprises a piston and cylinder, and wherein said vasodilating drug is stored in said cylinder portion.

18. A penile erection assist device for treating patients with impotence, comprising:

an implantable storage unit for storing physiologically active vasodilating material, said storage unit including an inlet configured to be accessible from outside the patient's body without surgery, said storage unit comprising a housing and a flexible diaphragm container sealed to and positioned within said housing to define a storage chamber for a vasodilating material;

fluid delivery means operatively associated with said storage unit;

at least one implantable thin sterile tubing hose in fluid communication with said storage unit and said fluid delivery means and having a proximal and distal end providing at least one delivery pathway, wherein said distal end is configured to be positioned adjacent penile erection tissue for delivering the vasodilating material thereto;

a control unit operatively associated with said fluid delivery means for controlling the delivery of said vasodilating material stored in said storage unit, said control unit including a plurality of sensors for detecting and monitoring operational parameters of said device;

a user interface unit positioned remote from said storage unit operatively associated with said control unit and accessible by a patient to allow adjustment or activation of said device and for providing input/output communications therebetween; and a secondary fluid pathway individually activatable separate from the delivery pathway for serially recirculating a test dosage through said storage unit and said fluid delivery means, and then returns the test dosage to said storage unit.

19. A penile erection assist device according to claim 18, wherein said control unit determines the amount of vasodilating material remaining in said storage unit responsive to one of pressure and displacement of said vasodilating material inside said diaphragm container and then displays the results on said interface unit.

20. A penile erection assist device according to claim 18, wherein said control unit generates a warning when the amount of said vasodilating material is below a predetermined level.

21. A penile erection assist device according to claim 18, wherein said control unit monitors and detects discrepancies between a predetermined dosage level of said vasodilating material and the amount delivered to the penile erectile tissues and communicates the information to the patient.

22. A penile erection assist device according to claim 18, wherein said storage unit comprises:

a septum entry port for receiving a needle to deliver a predetermined dosage of said vasodilating material into said diaphragm container; and a needle advancement stop positioned adjacent said septum entry port configured to allow delivery of a fluid from the needle into said housing and diaphragm and to prevent the needle from advancing beyond said stop to protect said diaphragm container from damage due to excess needle penetration.

23. A penile erection assist device according to claim 18, wherein said fluid delivery means and said storage unit are configured to define an integral unit.

24. A penile erection assist device according to claim 23, wherein said integral unit comprises a piston and cylinder, and wherein said vasodilating drug is stored in said cylinder portion.

* * * * *